United States Patent
Fukuzawa et al.

(10) Patent No.: US 9,244,007 B2
(45) Date of Patent: Jan. 26, 2016

(54) APPARATUS AND METHOD FOR MEASURING DEGREE OF CURE OF ADHESIVE AGENT

(71) Applicant: Nippon Sheet Glass Company, Limited, Minato-ku, Tokyo (JP)

(72) Inventors: Takashi Fukuzawa, Tokyo (JP); Hiroyuki Tanaka, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 0 days.

(21) Appl. No.: 14/081,822

(22) Filed: Nov. 15, 2013

(65) Prior Publication Data

US 2014/0071454 A1    Mar. 13, 2014

Related U.S. Application Data

(62) Division of application No. 13/530,634, filed on Jun. 22, 2012, now abandoned.

(30) Foreign Application Priority Data

Jun. 24, 2011   (JP) .................... 2011-141126
Jun. 24, 2011   (JP) .................... 2011-141127

(51) Int. Cl.
*G01N 21/41* (2006.01)
*G01N 21/47* (2006.01)
*G01N 21/43* (2006.01)

(52) U.S. Cl.
CPC .............. *G01N 21/47* (2013.01); *G01N 21/431* (2013.01); *G01N 2021/432* (2013.01)

(58) Field of Classification Search
None
See application file for complete search history.

(56) References Cited

U.S. PATENT DOCUMENTS

| | | | |
|---|---|---|---|
| 4,883,354 A * | 11/1989 | Sun et al. | 356/128 |
| 2009/0257046 A1* | 10/2009 | Dean et al. | 356/51 |
| 2011/0164255 A1* | 7/2011 | Konno et al. | 356/479 |

FOREIGN PATENT DOCUMENTS

| | | | |
|---|---|---|---|
| JP | 56-137135 A | 10/1981 |
| JP | 02-103448 A | 4/1990 |
| JP | 02-229741 A | 9/1990 |
| JP | 03-105233 A | 5/1991 |
| JP | 06-011442 A | 1/1994 |
| JP | 11-160155 A | 6/1999 |
| JP | 2006-275599 A | 10/2006 |
| JP | 2006-317282 A | 11/2006 |
| JP | 2007-248431 A | 9/2007 |
| WO | 2010/029935 A1 | 3/2010 |

OTHER PUBLICATIONS

Communication dated May 27, 2014 issued by the Japanese Patent Office in counterpart Japanese application No. 2011-141126.
Communication dated May 27, 2014 issued by the Japanese Patent Office in counterpart Japanese application No. 2011-141127.
M. Giordano et al., "Advanced cure monitoring by optoelectronic multifunction sensing system", Thin Solid Films, 2004, pp. 191-194.

* cited by examiner

*Primary Examiner* — Tri T Ton
(74) *Attorney, Agent, or Firm* — Sughrue Mion, PLLC

(57) ABSTRACT

A degree of cure measuring apparatus has: a second optical fiber for emitting light from a tip face thereof; a probe for holding adhesive agent and irradiating the adhesive agent with light while the adhesive agent is in contact with the tip face of the second optical fiber; a detector for detecting light that is reflected from an interface between the tip face of the second optical fiber and the adhesive agent and then returns to the second optical fiber; and a computer for calculating the refractive index of the adhesive agent from the rate of the light amount of the light detected by the detector to the emission light amount from the tip face of the second optical fiber.

7 Claims, 18 Drawing Sheets

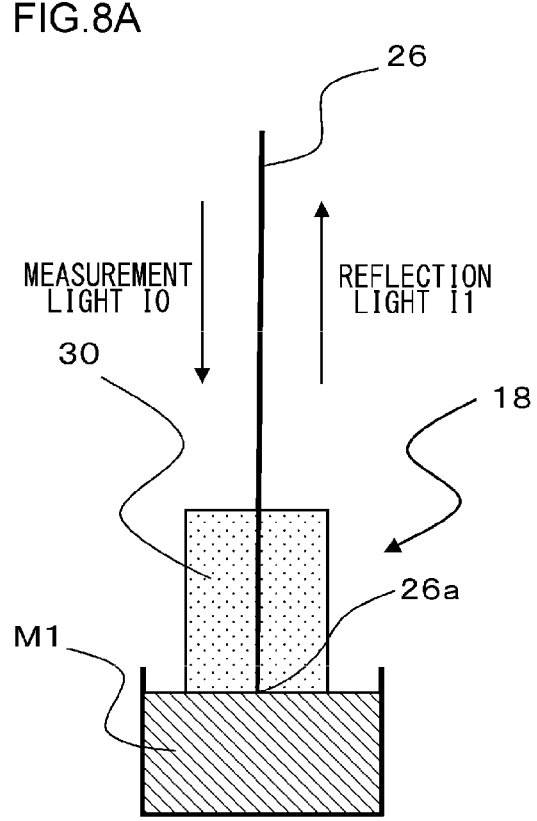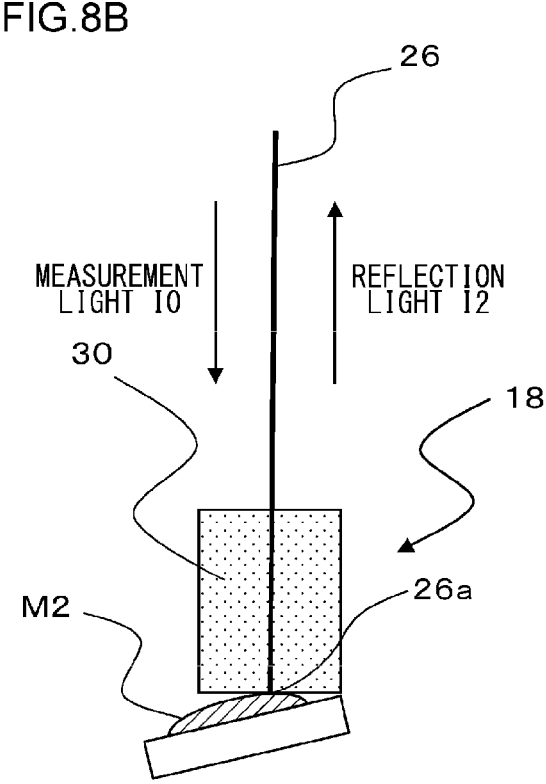

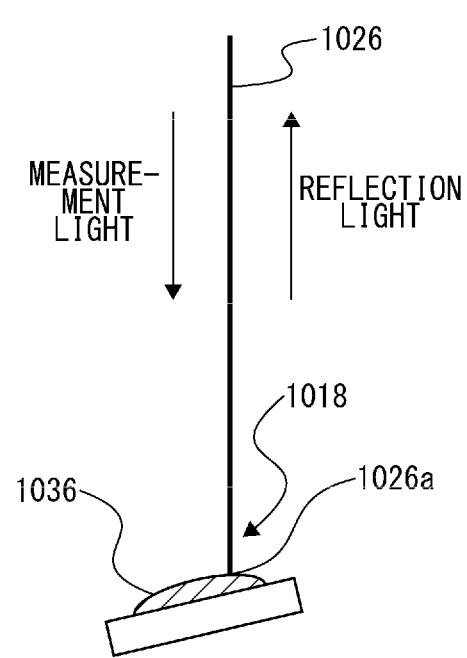
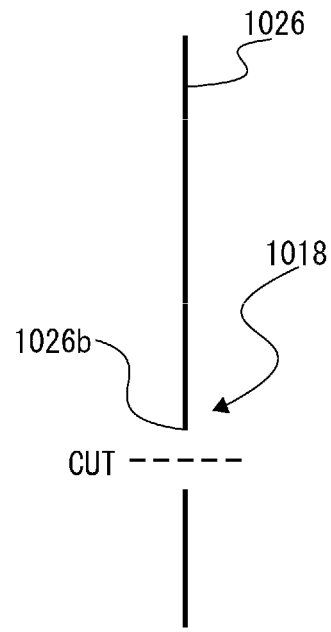

APPARATUS AND METHOD FOR MEASURING DEGREE OF CURE OF ADHESIVE AGENT

This application is a Divisional of U.S. application Ser. No. 13/530,634, filed Jun. 22, 2012, which claims priority to Japanese Application No. 2011-141126, filed Jun. 24, 2011, and Japanese Application No. 2011-141127, filed Jun. 24, 2011, the disclosure of each is incorporated herein by reference.

BACKGROUND OF THE INVENTION

1. Field of the Invention

The present invention relates to a apparatus and a method for measuring the degree of cure of adhesive agent.

2. Description of the Related Art

Adhesive agent such as epoxy type adhesive agent has been used in an assembling process of optical device or electronic device. It is necessary to measure the degree of cure of adhesive agent in a production process using such adhesive agent for the purpose of (1) grasping the temperature and time at which adhesive agent cures and determining a cure condition; (2) checking whether adhesive agent is cured as expected under a specified temperature and time condition when adhesive production lot is changed; and (3) checking whether adhesive agent is cured as expected under a specified temperature and time condition when the adhesive agent has been stocked for a long term.

(1) An FT-IR method (see JP-A-2007-248431, for example), (2) a DSC method (see JP-A-2-229741, for example) and (3) a method of measuring the degree of cure with a micro-hardness tester (see JP-A-3-105233) and the like are known as a method of measuring the degree of cure of adhesive agent.

[Patent Document 1] JP-A-2007-248431
[Patent Document 2] JP-A-2-229741
[Patent Document 3] JP-A-3-105233

With respect to the FT-IR method, it is necessary to prepare many samples under different temperature and time conditions and measure all of these samples. Therefore, much time and efforts are necessary, and also an available measuring apparatus is expensive. With respect to the DSC method, much time is taken to prepare and measure samples, and also it is impossible to grasp the relationship between temperature and curing time. With respect to the method with the micro-hardness tester, it is necessary to prepare many samples cured under different temperature and time conditions and also measure all of these samples; therefore, much time and efforts are necessary. In addition, this method has a problem that it is difficult to quantify a measurement result.

SUMMARY OF THE INVENTION

The present invention has been made in view of such circumstances, and an object of the present invention is to provide a apparatus and a method that can measure the degree of cure of adhesive agent.

In order to solve the problem, according to an aspect of the present invention, there is provided a degree of cure measuring apparatus for measuring a degree of cure of adhesive agent, including an optical fiber for emitting light from a tip face thereof, a probe for holding the adhesive agent therein and emitting light to the adhesive agent while the adhesive agent is in contact with the tip face of the optical fiber, a detector for detecting light returning from an interface between the tip face of the optical fiber and the adhesive agent to the optical fiber, and a refractive index calculator for calculating a refractive index of the adhesive agent from a rate of a light amount detected by the detector to an emission light amount from the tip face of the optical fiber.

The optical fiber may be a single mode optical fiber.

The probe may have a capillary provided to a tip portion of the optical fiber and a cylindrical member in which the capillary is inserted, and an inner wall surface of the cylindrical member, a tip face of the capillary and the tip face of the optical fiber may form an adhesive agent holding space for holding the adhesive agent.

The probe further may have an enclosing member for enclosing the adhesive agent in the adhesive agent holding space, a surface of the enclosing member that faces the tip face of the optical fiber being tilted at a predetermined angle with respect to the tip face of the optical fiber.

The probe further may have a capillary provided to a tip portion of the optical fiber, the capillary having a recess portion for holding the adhesive agent that is formed at a tip portion thereof.

A degree of cure measuring apparatus may have a recorder for recording time-variation of the refractive index calculated by the refractive index calculator.

Another aspect of the present invention, there is provided a degree of cure measuring method for measuring a degree of cure of adhesive agent, including emitting light from a tip face of an optical fiber, bringing the tip face of the optical fiber into contact with the adhesive agent, detecting light returning from an interface between the tip face of the optical fiber and the adhesive agent to the optical fiber, and comprising calculating a refractive index of the adhesive agent from a rate of a detected light amount to an emission light amount from the tip face of the optical fiber.

According to further another aspect of the present invention, there is provided a degree of cure measuring apparatus for measuring a degree of cure of adhesive agent, including an optical fiber for emitting light from a tip face thereof, a light guide member detachably connected to the optical fiber and for irradiating the adhesive agent with light while a light emission face thereof is in contact with the adhesive agent, and a detector for detecting light returning from an interface between the light emission face of the light guide member and the adhesive agent to the light guide member.

The light guide member may have an optical fiber piece connected to the tip face of the optical fiber.

The light guide member may have a lens that is configured to emit light incident from the optical fiber as parallel light.

The light guide member may have a lens that is configured so that light incident from the optical fiber is focused onto a light emission face thereof.

The light guide member may have a light guide part for irradiating the adhesive agent with light incident thereto while a light emission face thereof is in contact with the adhesive agent, and that is formed of a material having substantially the same refractive index as the adhesive agent before cure.

The light guide member further may have a lens provided between the optical fiber and the light guide part.

The degree of cure measuring apparatus may include a refractive index calculator for calculating a refractive index of the adhesive agent from a rate of a light amount detected by the detector to an emission light amount from the light guide member.

The degree of cure measuring apparatus may include a recorder for recording time-variation of the refractive index calculated by the refractive index calculator. Furthermore the degree of cure measuring apparatus may include a computer comprising a refractive index calculator and a recorder for recording time-change of the refractive index.

The optical fiber may be a single mode optical fiber.

The light guide member may have an adhesive agent holder for holding the adhesive agent.

According to further another aspect of the present invention, there is provided a degree of cure measuring method for measuring a degree of cure of adhesive agent, including bringing a tip face of an optical fiber into contact with the adhesive agent, emitting light from the tip face of the optical fiber to the adhesive agent, detecting light returning from an interface between the tip face of the optical fiber and the adhesive agent to the optical fiber, and forming a new tip face of the optical fiber after the degree of cure is measured.

The step of forming the tip face may include cutting the optical fiber and polishing a new tip face formed by cutting the optical fiber.

BRIEF DESCRIPTION OF THE DRAWINGS

FIGS. 8A and 8B are diagrams illustrating a refractive index measuring apparatus according to a second embodiment of the present invention;

FIGS. 17A and 17B are diagrams illustrating a degree of cure measuring method according to the third embodiment of the present invention.

DETAILED DESCRIPTION OF THE INVENTION

The invention will now be described by reference to the preferred embodiments. This does not intend to limit the scope of the present invention, but to exemplify the invention.

A degree of cure measuring apparatus for adhesive agent according to an embodiment of the present invention will be described.

First Embodiment

Figure 1:
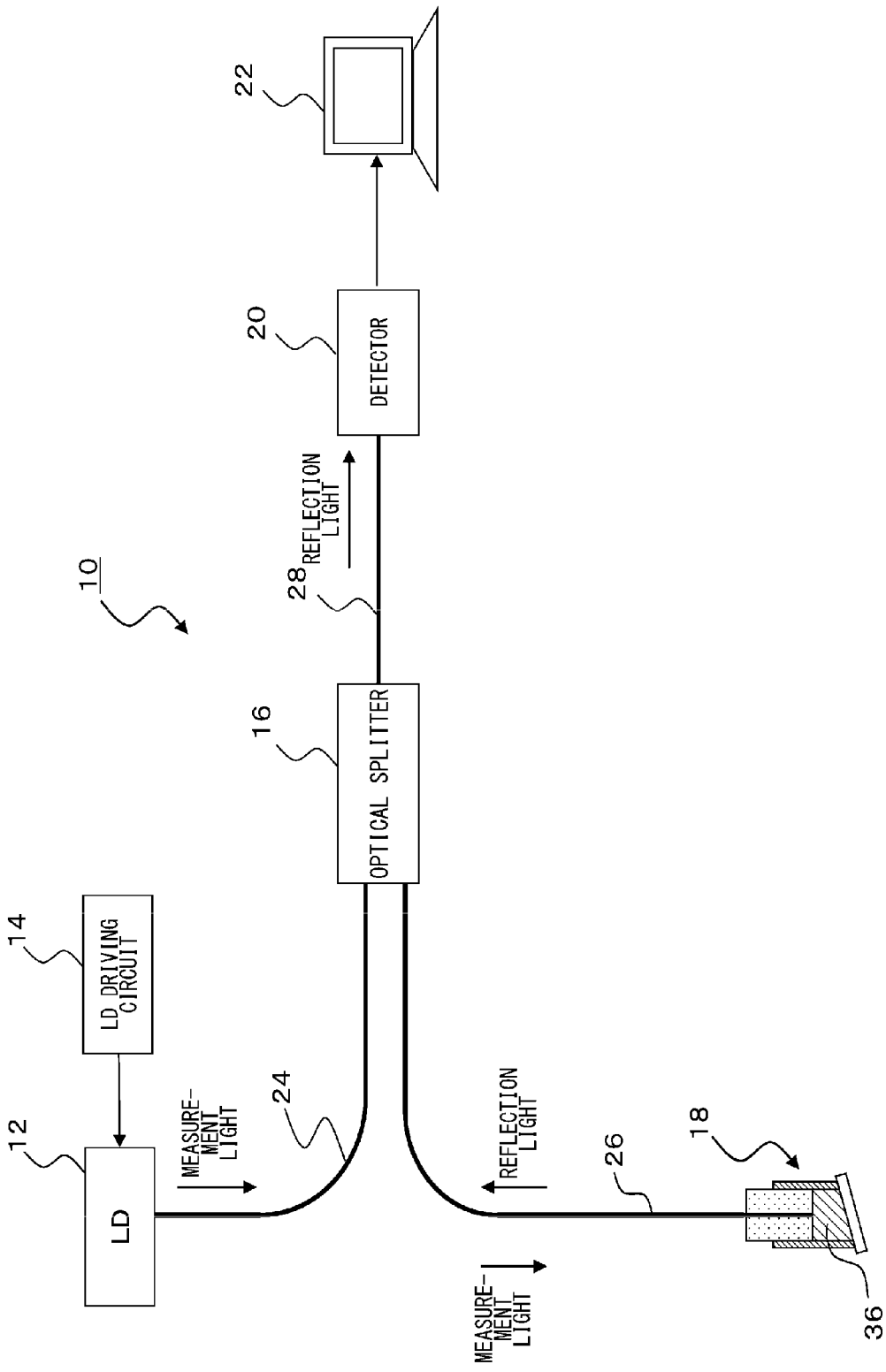
FIG. 1 is a diagram illustrating a degree of cure measuring apparatus according to a first embodiment of the present invention.

FIG. 1 is a diagram illustrating a degree of cure measuring apparatus 10 according to a first embodiment of the present invention. As illustrated in FIG. 1, the degree of cure measuring apparatus 10 has a laser diode (LD: Laser Diode) 12, an LD driving circuit 14 for driving the laser diode 12, an optical splitter 16, a probe 18, a detector 20, a first optical fiber 24 by which the laser diode 12 and the optical splitter 16 are connected to each other, a second optical fiber 26 by which the optical splitter 16 and the probe 18 are connected to each other, a third optical fiber 28 by which the optical splitter 16 and the detector 20 are connected to each other, and a computer 22 connected to the detector 20. The degree of cure measuring apparatus 10 is a apparatus for measuring the degree of cure of adhesive agent 36 held in the probe 18.

The laser diode 12 emits measurement light to be applied to the adhesive agent 36, and a laser diode having an emission center wavelength of 1,550 nm may be used as the laser diode 12, for example. The power of the measurement light emitted from the laser diode 12 is controlled by the LD driving circuit 14.

The measurement light emitted from the laser diode 12 passes through the first optical fiber 24, and is input to the optical splitter 16. A single mode optical fiber is suitably used as the first optical fiber 24.

The optical splitter 16 has a function of outputting light input from the first optical fiber 24 to the second optical fiber 26 and outputting light input from the second optical fiber 26 to the third optical fiber 28. Accordingly, measurement light input from the laser diode 12 to the optical splitter 16 through the first optical fiber 24 propagates through the second optical fiber 26, and then is emitted from the probe 18 provided to the tip of the second optical fiber 26. A single mode optical fiber is suitably used as the second optical fiber 26 as in the case of the first optical fiber 24.

Figure 2:
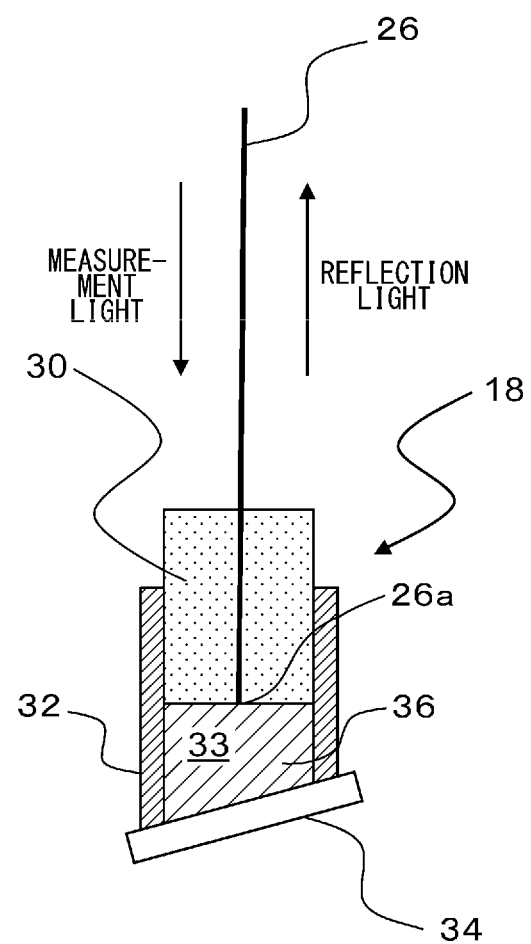
FIG. 2 is a diagram illustrating the structure of a probe.

FIG. 2 is a diagram illustrating the structure of the probe 18. As illustrated in FIG. 2, the probe 18 has a capillary 30 provided to a tip portion of the second optical fiber 26, a cylindrical glass pipe 32 in which the capillary 30 is inserted, and a glass plate 34 provided to a tip portion of the glass pipe 32.

The capillary 30 is a cylindrical member having a minute through hole formed at the center thereof, and the second optical fiber 26 is inserted in the through hole. A tip face of the capillary 30 and a tip face 26a of the second optical fiber 26 are arranged within the same plane so as to be vertical to the axis of the second optical fiber 26. The capillary 30 is inserted in the glass pipe 32 by about half of the whole length of the glass pipe 32. A space 33 for holding the adhesive agent 36 (referred to as "adhesive agent holding space") is formed by an inner wall surface of the glass pipe 32, the tip face of the capillary 30 and the tip face 26a of the second optical fiber 26. The glass plate 34 is provided so as to block an opening of the adhesive agent holding space 33, and the adhesive agent 36 is enclosed in the adhesive agent holding space 33.

In this embodiment, the adhesive agent 36 is filled in the adhesive agent holding space 33. Accordingly, the tip face 26a of the second optical fiber 26 and the adhesive agent 36 are brought into contact with each other. Under this state, measurement light is applied from the tip face 26a of the second optical fiber 26 to the adhesive agent 36. The measurement light is reflected from the interface between the adhesive agent 36 and the tip face 26a of the second optical fiber 26, and then incident from the tip face 26a into the core of the second optical fiber 26. The reflection light returning from the interface between the adhesive agent 36 and the tip face 26a to the second optical fiber 26 is input to the optical splitter 16.

Here, in this embodiment, a surface of the glass plate 34 that faces the tip face 26a of the second optical fiber 26 is tilted at a predetermined angle with respect to the tip face 26a of the second optical fiber 26. This is because light passing through the adhesive agent 36 and reflecting from the glass plate 34 is prevented from returning to the core of the second optical fiber 26.

Returning to FIG. 1, the reflection light input from the second optical fiber 26 is output to the third optical fiber 28 by the optical splitter 16. A single mode optical fiber is suitably used as the third optical fiber 28 as in the case of the first optical fiber 24 and the second optical fiber 26.

The detector 20 detects the light amount of the reflection light input from the third optical fiber 28, and outputs the detection result to the computer 22. A photodiode or the like is suitably used as the detector 20.

Figure 3:
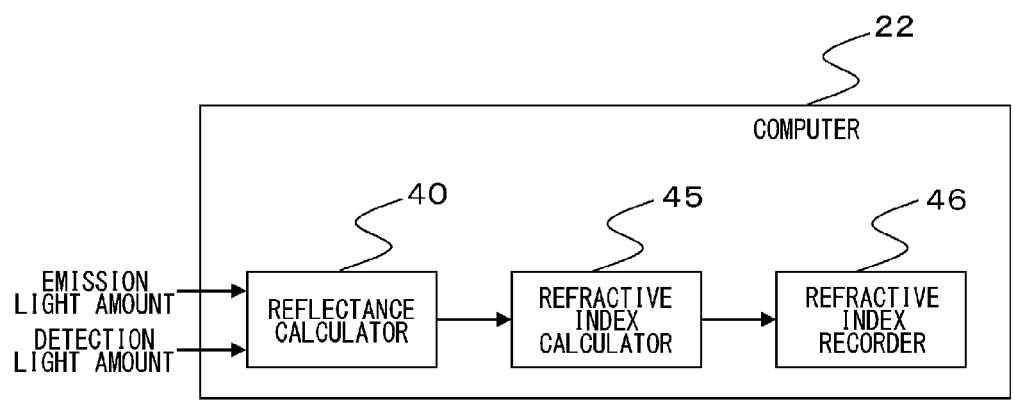
FIG. 3 is a diagram illustrating functional blocks of a computer.

FIG. 3 is a diagram illustrating functional blocks of the computer 22. As illustrated in FIG. 3, the computer 22 has a reflectance calculator 40, a refractive index calculator 45 and a refractive index recorder 46. The respective blocks described in this specification are obtained in a hardware style (on a hardware basis) by elements such as a CPU of a computer or mechanical devices or obtained in a software style (on a software basis) by computer programs and the like. In FIG. 3, functional blocks obtained by the cooperation of these elements are illustrated. Accordingly, it is understandable by persons skilled in the art that these functional blocks can be obtained in various styles by the combination of software and hardware elements.

The light amount of reflection light detected by the detector 20 is input to the reflectance calculator 40. The emission light amount (the light amount of measurement light) from the tip face 26a of the second optical fiber 26 is also input to the reflectance calculator 40. This emission light amount may be calculated from driving current of the laser diode 12. Furthermore, the emission light amount may be obtained by measuring an emission light amount from the tip face 26a in advance before the adhesive agent 36 is injected.

The reflectance calculator 40 calculates the rate of the detection light amount I2 detected by the detector 20 to the emission light amount I1 from the tip face 26a of the second optical fiber 26, that is, the reflectance BR at the interface between the adhesive agent 36 and the tip face 26a of the second optical fiber 26. A calculating formula for the reflectance BR is represented by the following formula (1).

[Formula 1]

$$BR = 10\log_{10}\frac{I2}{I1} \quad (1)$$

The refractive index calculator 45 calculates the refractive index n of the adhesive agent 36 based on the reflectance BR calculated by the reflectance calculator 40. A calculating formula for the refractive index n of the adhesive agent 36 is represented by the following formula (2). The formula (2) can be derived by modifying Fresnel's reflectance formula.

[Formula 2]

$$n = -\frac{1+\sqrt{10^{\frac{BR}{10}}}}{1-\sqrt{10^{\frac{BR}{10}}}} \times n' \quad (2)$$

In the formula (2), n' represents the refractive index of the core of the second optical fiber 26.

The refractive index recorder 46 records the time-variation of the refractive index calculated by the refractive index calculator 45. The refractive index recorder 46 may output the thus-recorded time-variation of the refractive index to a paper medium or display the recorded time-variation on a display. The degree of cure of the adhesive agent 36 can be grasped by obtaining the time-variation of the refractive index.

Figure 4:
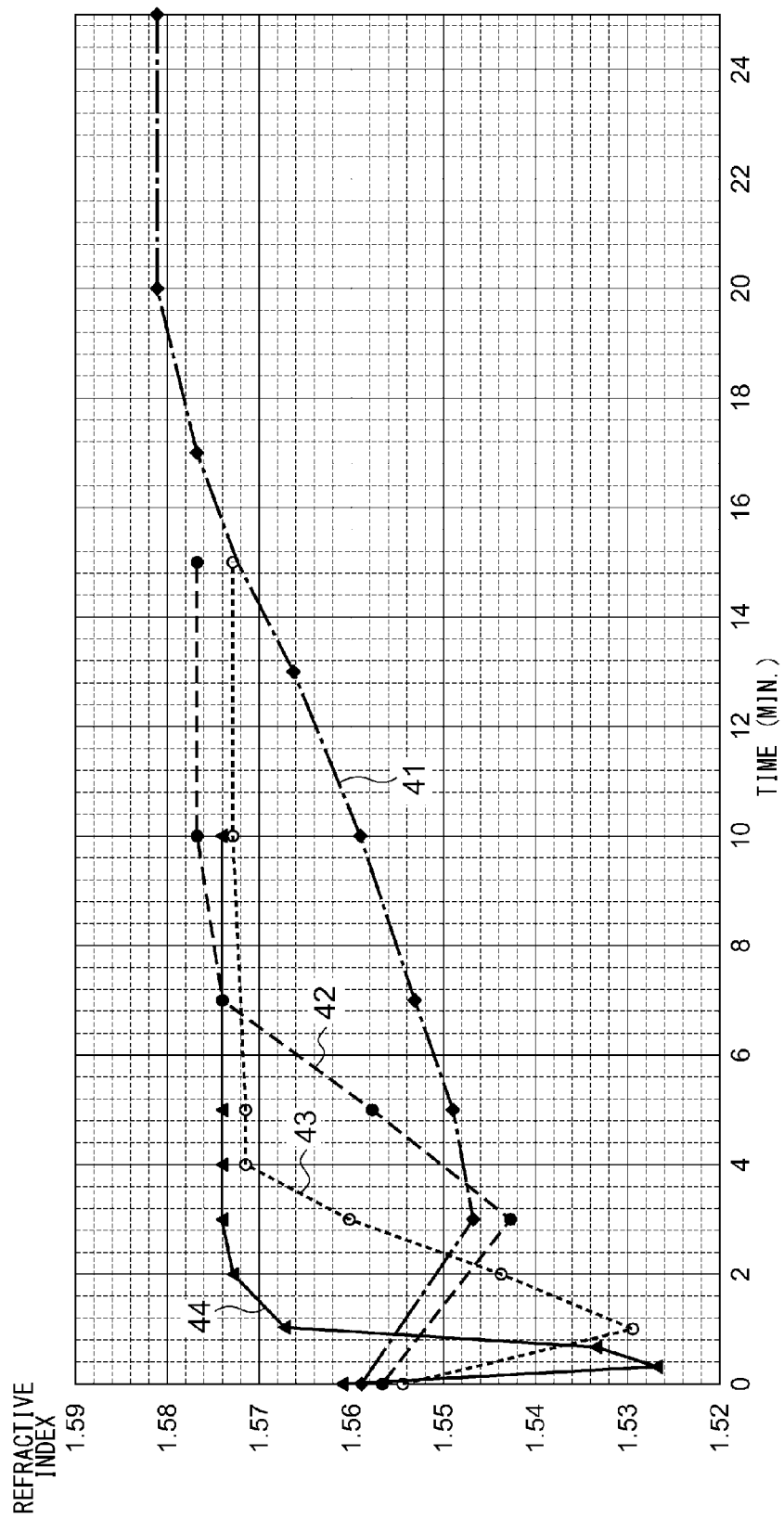
FIG. 4 is a diagram showing examples of time-variation of refractive indices.

FIG. 4 shows examples of the time-variation of the refractive indices. Specifically, FIG. 4 shows the time-variation of the refractive index obtained when Adhesive Epo-Tek® 353ND produced by Epoxy Technology Company (hereinafter referred to as adhesive agent 1) is used as the adhesive agent. In FIG. 4, the vertical axis represents the refractive index, and the horizontal axis represents the time (minute) from the start of curing of the adhesive agent. Standard curing conditions of the adhesive agent 1 are 80° C.—30 minutes, 100° C.—10 minutes, 120° C.—5 minutes and 150° C.—1 minute.

After the adhesive agent 1 is enclosed in the adhesive agent holding space 33 of the probe 18 as illustrated in FIG. 2, the probe 18 is put into a furnace whose temperature was raised to a predetermined temperature, and variation of the refractive index with time lapse is measured. In FIG. 4, a dashed line 41 represents the time-variation of the refractive index of the adhesive agent 1 at the furnace temperature=80° C., a long dotted line 42 represents the time-variation of the refractive index of the adhesive agent 1 at the furnace temperature=90° C., a dotted line 43 represents the time-variation of the refractive index of the adhesive agent 1 at the furnace temperature=100° C., and a solid line 44 represents the time-variation of the refractive index of the adhesive agent 1 at the furnace temperature=120° C. The first to third optical fibers are single mode optical fibers, and the refractive index n' of the cores thereof is set to 1.46.

In FIG. 4, each of the curved lines 41 to 44 varies where the refractive index thereof increases with time lapse after the refractive index temporarily decreases, and then the refractive index becomes constant when some time elapses. The time period from the time at which curing of the adhesive agent 1 starts till the time at which the refractive index becomes constant is different among the curves. When the degree of cure of the adhesive agent 1 is measured at the time point when the refractive index becomes constant, the degree of cure reaches a predetermined degree of cure. Accordingly, the time period from the start time of curing till the time at which the refractive index becomes constant can be determined as a curing completion time for the adhesive agent 1. The curing completion time obtained from FIG. 4 is substantially coincident with the standard curing condition described above.

Figure 5:
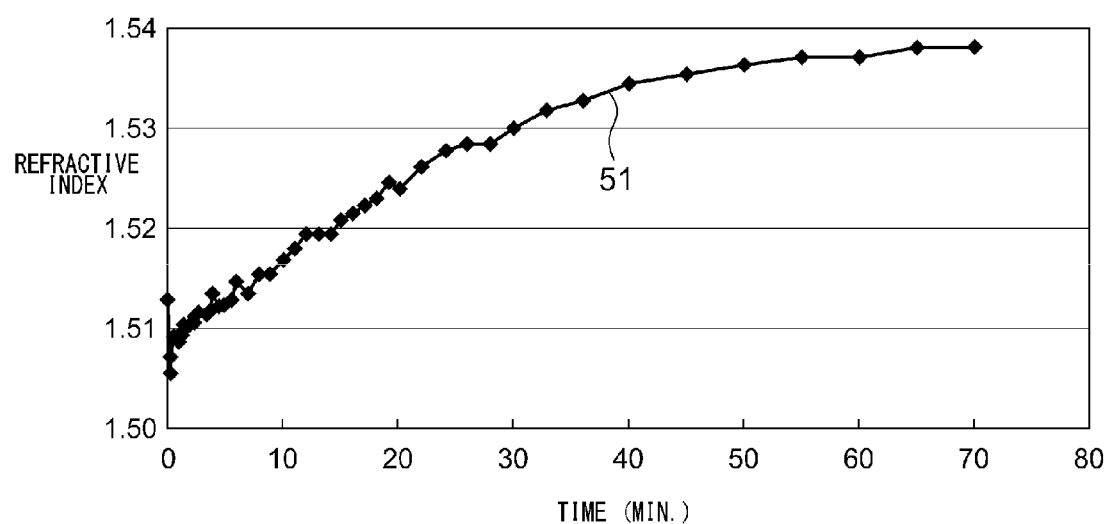
FIG. 5 is a diagram showing another example of time-variation of refractive index.

FIG. 5 shows another example of time-variation of the refractive index. Specifically, FIG. 5 shows the time-variation of the refractive index obtained when Adhesive Epo-Tek® 301-2 produced by Epoxy Technology Company (hereinafter referred to as adhesive agent 2) is used as the adhesive agent. The standard curing condition of the adhesive agent 2 is 80° C.—3 hours.

As in the case of the adhesive agent 1, after the adhesive agent 2 is enclosed in the adhesive agent holding space 33 of the probe 18, the probe 18 is put into a furnace whose temperature was raised to a predetermined temperature, and the variation of the refractive index of the adhesive agent 2 with time lapse is measured. In FIG. 5, a curved line 51 represents a time-variation of the refractive index at the furnace temperature of 80° C.

As shown in FIG. 5, the curved line 51 varies where after the refractive index temporarily decreases, the refractive index increases with time lapse and then becomes constant when about 65 minutes elapses from start of curing. When the degree of cure of the adhesive agent 2 is measured at the time point when the refractive index becomes constant, the degree of cure reaches a predetermined degree of cure. Accordingly, the time period from the time when curing starts till the time when the refractive index becomes constant can be determined as a curing completion time for the adhesive agent 2.

As described above, according to the degree of cure measuring apparatus 10 of this embodiment, the curing completion time of the adhesive agent can be measured with high precision by measuring the time-variation of the refractive index of the adhesive agent. According to the degree of cure measuring apparatus 10, the time-variation of the degree of cure of the adhesive agent can be measured, and information as to how long it takes to cure the adhesive agent by about 50% of degree of cure can be obtained, for example.

As described above, a single mode optical fiber is preferably used as the second optical fiber 26 used for the probe 18. Since the single mode optical fiber has a small core diameter of 10 μm or less, light other than light reflected from the interface between the tip face 26a of the second optical fiber 26 and the adhesive agent 36 (light which is temporarily incident into the adhesive agent 36 and then irregularly reflected or the like) is hardly incident. Accordingly, the refractive index of the adhesive agent 36 can be stably measured.

In the above embodiment, the adhesive agent 36 is enclosed in the adhesive agent holding space 33 by using the glass plate 34. However, the tip face 26a of the second optical fiber 26 and the adhesive agent can be kept in contact with each other without providing the glass plate 34 insofar as the probe 18 is set while the open face of the adhesive agent holding space 33 faces the vertically upper side.

Figure 6:
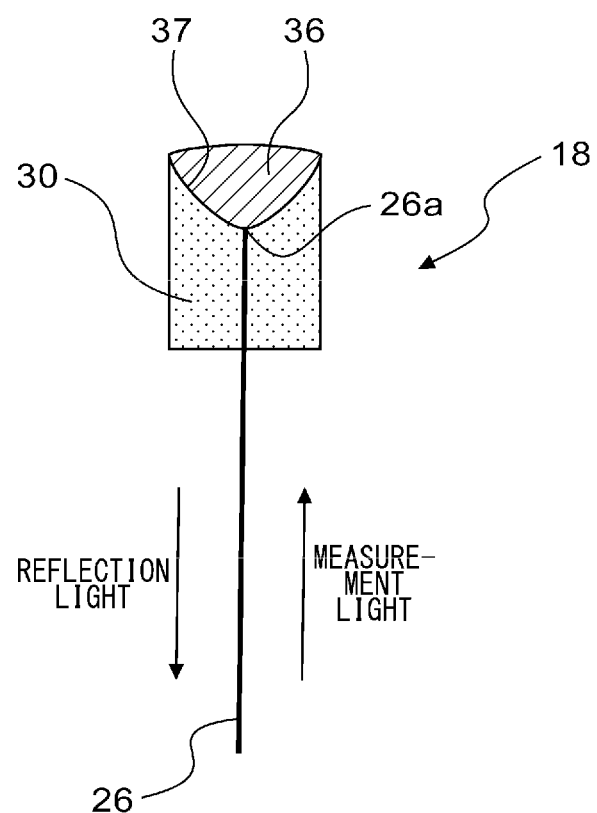
FIG. 6 is a diagram illustrating a modification of the probe.

FIG. 6 illustrates a modification of the probe 18. In this modification, the tip portion of the second optical fiber 26 is provided with the capillary 30. A recess portion 37 for holding the adhesive agent 36 is formed at the tip portion of the capillary 30. The tip face 26a of the second optical fiber 26 is exposed to the internal space of the recess portion 37. For example, the bottom surface of the recess portion 37 and the tip face 26a of the second optical fiber 26 may be arranged on the same plane.

When the adhesive agent 36 is injected into the recess portion 37 in the thus-formed probe 18, the tip face 26a of the second optical fiber 26 and the adhesive agent 36 come into contact with each other. Accordingly, as in the case of the probe described with reference to FIG. 2, light reflected from the interface between the tip face 26a of the second optical fiber 26 and the adhesive agent 36 can be detected.

Figure 7:
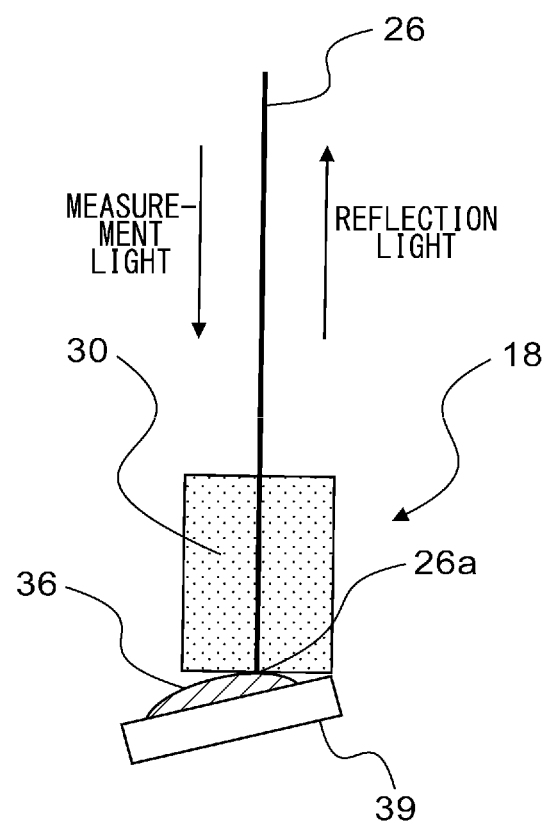
FIG. 7 is a diagram illustrating another modification of the probe.

FIG. 7 illustrates another modification of the probe 18. The probe 18 according to this modification is configured so that the capillary 30 is provided to the tip portion of the second optical fiber 26. The tip face of the capillary 30 and the tip face 26a of the second optical fiber 26 are arranged on the same plane.

The probe 18 of this modification is can be used to measure the degree of cure of the adhesive agent 36 placed on the glass plate 39, for example. In this modification, the probe 18 is disposed so that the tip face 26a of the second optical fiber 26 comes into contact with the adhesive agent 36, whereby light reflected from the interface between the tip face 26a of the second optical fiber 26 and the adhesive agent 36 can be detected.

In this modification, the glass plate 39 is preferably tilted at a predetermined angle with respect to the tip face 26a of the second optical fiber 26. This is to prevent light reflected from the glass plate 39 from returning to the core of the second optical fiber 26.

Second Embodiment

FIGS. 8A and 8B are diagrams illustrating a refractive index measuring apparatus according to a second embodiment of the present invention. The refractive index measuring apparatus according to this embodiment is a apparatus for measuring the absolute refractive index of a material.

The refractive index measuring apparatus according to this embodiment has a similar structure to the degree of cure measuring apparatus 10 illustrated in FIG. 1. In this embodiment, the probe 18 is configured so that the capillary 30 is provided to the tip portion of the second optical fiber 26. The tip face of the capillary 30 and the tip face 26a of the second optical fiber 26 are arranged on the same plane. A method of measuring the absolute refractive index by using the refractive index measuring apparatus according to this embodiment will be described below.

First, as illustrated in FIG. 8A, the tip face 26a of the second optical fiber 26 is brought into contact with a material M1 whose absolute refractive index is known, and the material M1 is irradiated with measurement light. The material M1 may be air (absolute refractive index=1) or water (absolute refractive index=1.33), for example. Reflection light reflecting from the interface between the material M1 and the tip face 26a and returning to the second optical fiber 26 is detected by a detector (not shown).

When the absolute refractive index of the core of the second optical fiber 26 is represented by nc, the absolute refractive index of the material M1 is represented by n1 and the light amount of measurement light is represented by I0, the light amount I1 of the reflection light is represented by the following formula (3) from the Fresnel's reflectance formula.

[Formula 3]

$$I1 = \left(\frac{nc - n1}{nc + n1}\right)^2 \times I0 \qquad (3)$$

Accordingly, by measuring the light amount I1 of the reflection light, the light amount I0 of the measurement light can be obtained from the following formula (4).

[Formula 4]

$$I0 = \frac{I1}{\left(\frac{nc - n1}{nc + n1}\right)^2} \qquad (4)$$

Subsequently, a material M2 whose absolute refractive index is unknown is irradiated with measurement light having the same light amount I0 as that applied to the material M1. When the absolute refractive index of the material M2 is represented by n2 and the light amount of the reflection light is represented by I2, the following formula (5) is satisfied from the Fresnel's reflectance formula.

[Formula 5]

$$I2 = \left(\frac{nc - n2}{nc + n2}\right)^2 \times I0 \quad (5)$$

Accordingly, by measuring the light amount I2 of the reflection light returning from the interface between the material M2 and the tip face 26a to the second optical fiber 26, the absolute refractive index n2 of the material M2 can be obtained from the formula (5).

In a case of adhesive agent containing much filler, light emitted from the optical fiber may irregularly reflected from the filler, and a part of the light may return to the optical fiber. In this case, the detected light amount is varied under uncured state; however, the variation is reduced as curing progresses. Accordingly, the degree of cure of the adhesive agent may be determined based on the fact that the variation in the detected light amount is nullified.

Furthermore, in the first and second embodiments, the degree of cure of the adhesive agent is measured by obtaining the time-variation of the refractive index of the adhesive agent. However, the degree of cure of the adhesive agent can be measured by obtaining the time-variation of light returning from the interface between the tip face of the optical fiber and the adhesive agent to the optical fiber.

Third Embodiment

Figure 9:
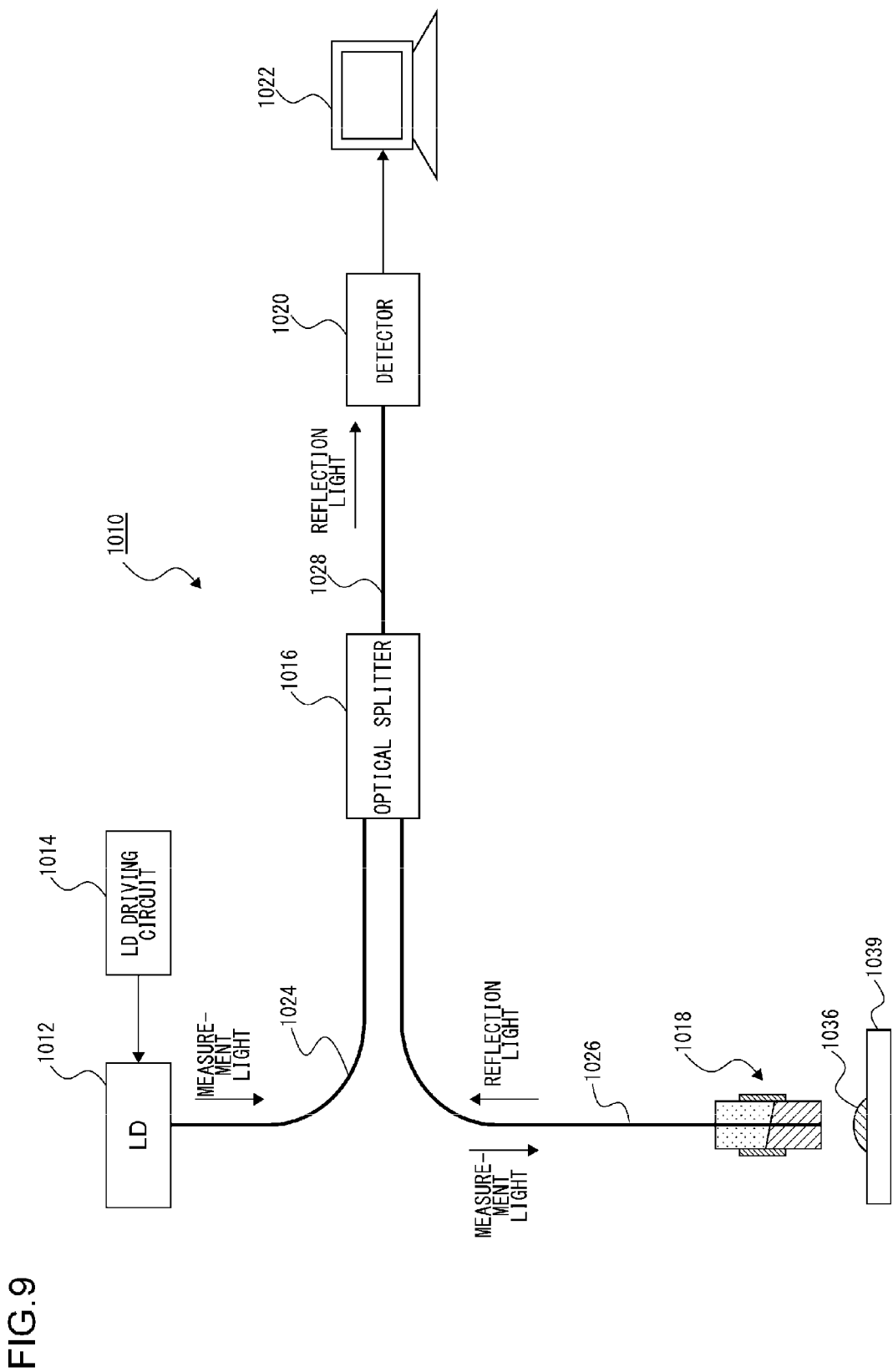
FIG. 9 is a diagram illustrating a degree of cure measuring apparatus according to a third embodiment of the present invention.

FIG. 9 is a diagram illustrating a degree of cure measuring apparatus according to a third embodiment of the present invention. As illustrated in FIG. 9, a degree of cure measuring apparatus 1010 has a laser diode (LD: Laser Diode) 1012, an LD driving circuit 1014 for driving the laser diode 1012, an optical splitter 1016, a probe 1018, a detector 1020, a first optical fiber 1024 by which the laser diode 1012 and the optical splitter 1016 are connected to each other, a second optical fiber 1026 by which the optical splitter 1016 and the probe 1018 are connected to each other, a third optical fiber 1028 by which the optical splitter 1016 and the detector 1020 are connected to each other, and a computer 1022 connected to the detector 1020. The degree of cure measuring apparatus 1010 is a apparatus for measuring the degree of cure of adhesive agent 1036 placed on a glass plate 1039.

The laser diode 1012 emits measurement light to be applied to the adhesive agent 1036, and a laser diode having an emission center wavelength of 1,550 nm may be used as the laser diode 1012, for example. The power of the measurement light emitted from the laser diode 1012 is controlled by the LD driving circuit 1014.

The measurement light emitted from the laser diode 1012 passes through the first optical fiber 1024 and is input to the optical splitter 1016. A single mode optical fiber is suitably used as the first optical fiber 1024.

The optical splitter 1016 has a function of outputting light input from the first optical fiber 1024 to the second optical fiber 1026, and outputting light input from the second optical fiber 1026 to the third optical fiber 1028. Accordingly, measurement light input from the laser diode 1012 to the optical splitter 1016 through the first optical fiber 1024 propagates through the second optical fiber 1026, and then is emitted from the probe 1018 provided to the tip of the second optical fiber 1026. A single mode optical fiber is suitably used as the second optical fiber 1026 as in the case of the first optical fiber 1024.

Figure 10:
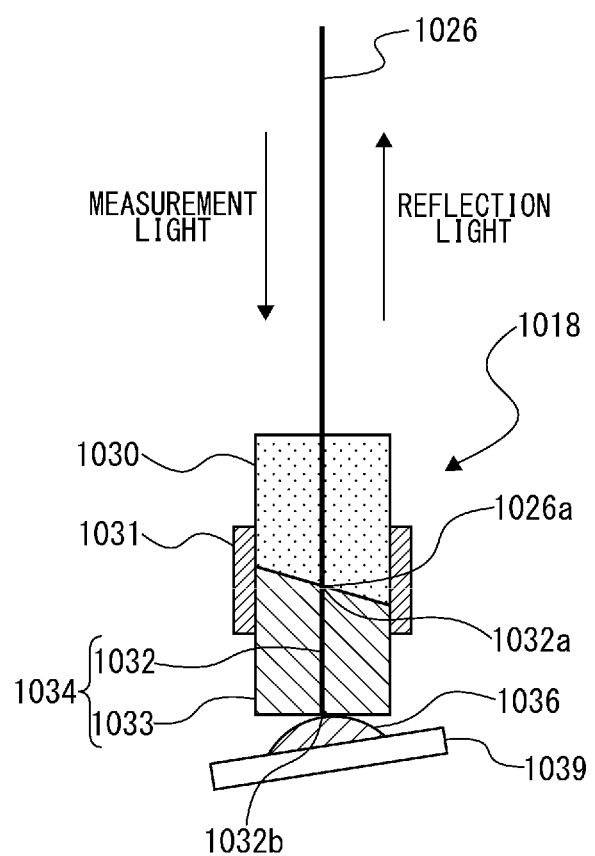
FIG. 10 is a diagram illustrating the structure of a probe.

FIG. 10 is a diagram illustrating the structure of the probe. As illustrated in FIG. 10, the probe 1018 has a capillary 1030 provided to a tip portion of the second optical fiber 1026, a light guide member 1034 provided at a front side of the capillary 1030, and a split sleeve 1031 for connecting the capillary 1030 and the light guide member 1034.

The capillary 1030 is a cylindrical member having a minute through hole formed at the center thereof, and the second optical fiber 1026 is inserted through the through hole. A tip face 1026a of the second optical fiber 1026 is configured as a slope surface tilted with respect to the axis of the second optical fiber 1026 to prevent light reflected from the joint point thereof with the light guide member 1034 from returning to the second optical fiber 1026. A tip face of the capillary 1030 is configured as a slope face which is arranged on the same plane as the tip face 1026a of the second optical fiber 1026.

The light guide member 1034 has an optical fiber piece 1032 and a capillary piece 1033. A single mode optical fiber is suitably used as the optical fiber piece 1032. In this case, it is preferable that the same optical fiber as the second optical fiber 1026 be used for the optical fiber piece 1032 from the viewpoint of a connecting efficiency. The capillary piece 1033 is a cylindrical member having a minute through hole formed at the center thereof, and the optical fiber piece 1032 is inserted through the through hole. A first end face 1032a of the optical fiber piece 1032 that is connected to the tip face 1026a of the second optical fiber 1026 is configured as a slope surface in accordance with the tip face 1026a of the second optical fiber 1026. Furthermore, a first end face of the capillary piece 1033 that faces the tip face of the capillary 1030 is configured as a slope surface arranged on the same plane as the first end face 1032a of the optical fiber piece 1032. A second end face 1032b of the optical fiber piece 1032 and a second end face of the capillary piece 1033 are formed on the same plane so as to be vertical to the axis of the optical fiber piece 1032.

The capillary 1030 and the capillary piece 1033 are inserted in the split sleeve 1031. The optical fiber piece 1032 with the capillary 1030 is detachably connected to the second optical fiber 1026 by the split sleeve 1031. Under a joint state, the tip face 1026a of the second optical fiber 1026 and the first end face 1032a of the optical fiber piece 1032 come into contact with each other, and measurement light emitted from the tip face 1026a of the second optical fiber 1026 is incident from the first end face 1032a of the optical fiber piece 1032 into the fiber, and emitted from the second end face 1032b at the opposite side.

After the degree of cure of the adhesive agent 1036 is measured, the probe 1018 is disposed so that the second end face 1032b of the optical fiber piece 1032 comes into contact with the adhesive agent 1036. Under this state, measurement light is applied from the second end face 1032b of the optical fiber piece 1032 to the adhesive agent 1036. This measurement light is reflected from the interface between the adhesive agent 1036 and the second end face 1032b of the optical fiber piece 1032, and then incident from the second end face 1032b to the core of the optical fiber piece 1032 again. Reflection light returning from the interface between the adhesive agent 1036 and the second end face 1032b to the optical fiber piece 1032 is input to the optical splitter 1016 through the second optical fiber 1026.

The glass plate 1039 on which the adhesive agent 1036 is placed is preferably tilted at a predetermined angle with respect to the second end face 1032b of the optical fiber piece 1032. This is to prevent light passing through the adhesive agent 1036 and reflecting from the glass plate 1039 from returning to the optical fiber piece 1032.

Returning to FIG. 9, the optical splitter 1016 outputs the reflection light input from the second optical fiber 1026 to the third optical fiber 1028. A single mode optical fiber is suitably used as the third optical fiber 1028 as in the case of the first optical fiber 1024 and the second optical fiber 1026.

The detector 1020 detects the light amount of reflection light input from the third optical fiber 1028, and outputs the detected light amount to the computer 1022. A photodiode or the like is suitably used as the detector 1020.

Figure 11:
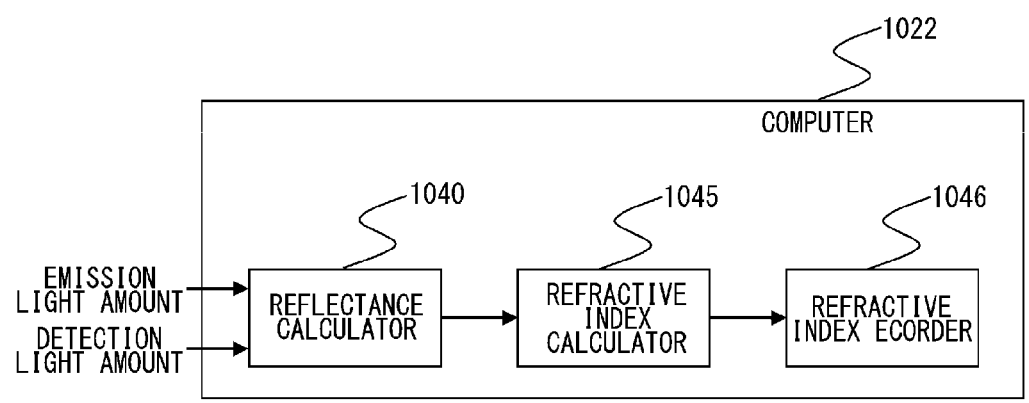
FIG. 11 is a diagram illustrating functional blocks of a computer.

FIG. 11 is a diagram illustrating functional blocks of the computer. As illustrated in FIG. 11, the computer 1022 has a reflectance calculator 1040, a refractive index calculator 1045 and a refractive index recorder 1046. The respective blocks described in this specification are obtained in a hardware style (on a hardware basis) by elements such as a CPU of a computer or mechanical devices or obtained in a software style (on a software basis) by computer programs and the like. In FIG. 11, functional blocks obtained by the cooperation of these elements are illustrated. Accordingly, it is understandable by persons skilled in the art that these functional blocks can be obtained in various styles by the combination of software and hardware elements.

The light amount of reflection light detected by the detector 1020 is input to the reflectance calculator 1040. The emission light amount (the light amount of measurement light) from the second end face 1032b of the optical fiber piece 1032 is input to the reflectance calculator 1040. This emission light amount may be obtained based on the driving current of the laser diode 1012. Furthermore, the emission light amount from the second end face 1032b may be measured in advance before measurement.

The reflectance calculator 1040 calculates the rate of the detected light amount I2 detected by the detector 1020 to the emission light amount I1 from the second end face 1032b of the optical fiber piece 1032, that is, the reflectance BR at the interface between the adhesive agent 1036 and the tip face 1026a of the second optical fiber 1026. The calculating formula for the reflectance BR is represented by the following formula (6).

[Formula 6]

$$BR = 10\log_{10}\frac{I2}{I1} \quad (6)$$

The refractive index calculator 1045 calculates the refractive index n of the adhesive agent 1036 based on the reflectance BR calculated by the reflectance calculator 1040. The calculating formula for the refractive index n of the adhesive agent 1036 is represented by the following formula (7). The formula (7) can be derived by modifying the Fresnel's reflectance formula.

[Formula 7]

$$n = -\frac{1+\sqrt{10^{\frac{BR}{10}}}}{1-\sqrt{10^{\frac{BR}{10}}}} \times n' \quad (7)$$

In the formula (7), n' represents the refractive index of the core of the second optical fiber 1026.

The refractive index recorder 1046 records the time-variation of the refractive index calculated by the refractive index calculator 1045. The refractive index recorder 1046 may output the recorded time-variation of the refractive index to a paper medium or display the time-variation on a display. The degree of cure of the adhesive agent 1036 can be grasped by obtaining the time-variation of the refractive index.

Figure 12:
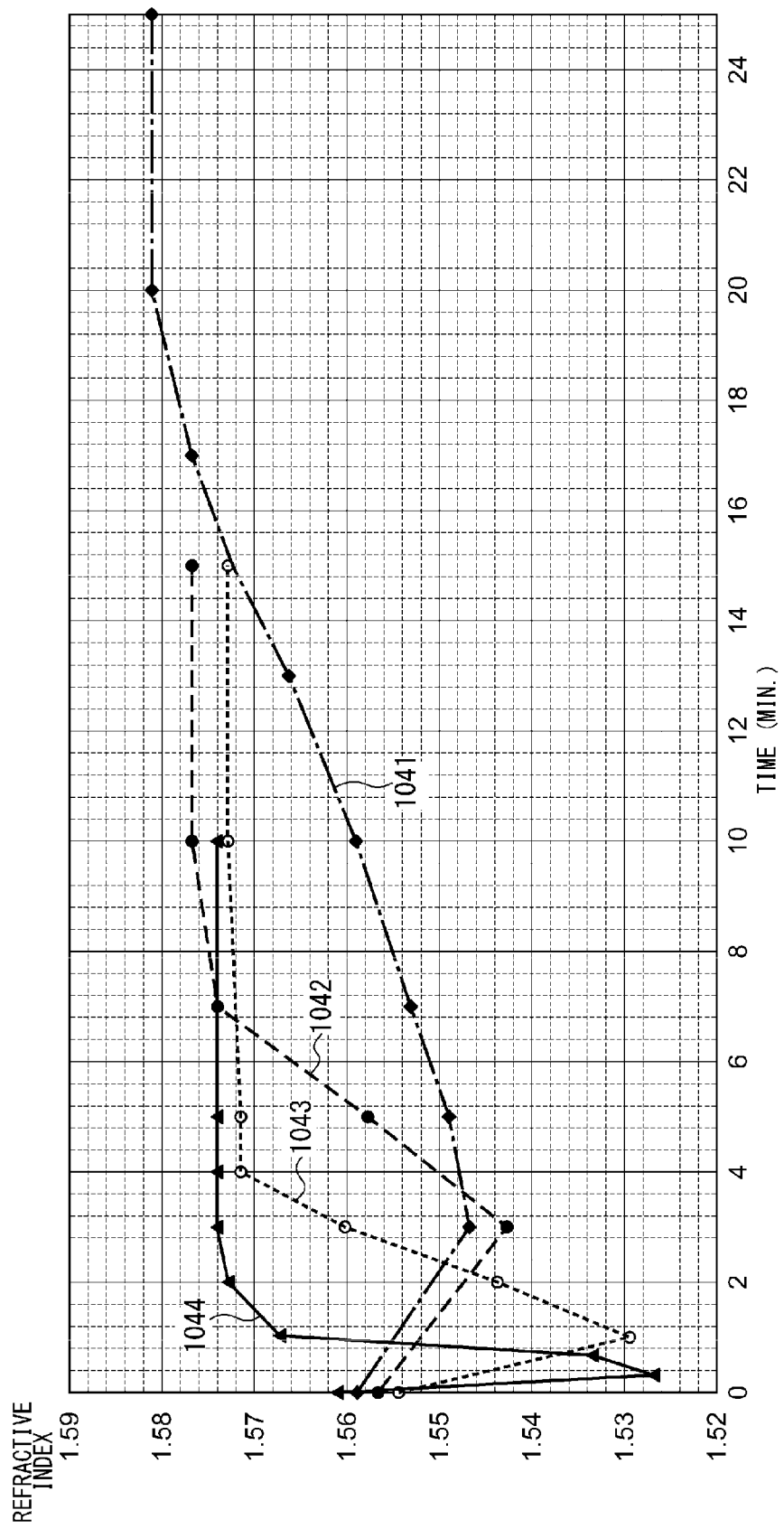
FIG. 12 is a diagram showing examples of time-variation of refractive indices.

FIG. 12 shows an example of the time-variation of the refractive index. Specifically, FIG. 12 shows the time-variation of the refractive index obtained when Adhesive Epo-Tek® 353ND produced by Epoxy Technology Company (hereinafter referred to as adhesive agent 1) is used as the adhesive agent. In FIG. 12, the vertical axis represents the refractive index, and the horizontal axis represents the time (minute) from start of curing. Standard curing conditions of the adhesive agent 1 are 80° C.—30 minutes, 100° C.—10 minutes, 120° C.—5 minutes and 150° C.—1 minute.

As illustrated in FIG. 10, after the probe 1018 is disposed on the adhesive agent 1036, the probe 1018 and the adhesive agent 1036 are put into a furnace whose temperature is increased to a predetermined temperature, and variation of the refractive index of the adhesive agent 1036 with time lapse is measured. In FIG. 12, a dashed line 1041 represents the time-variation of the refractive index at the furnace temperature of 80° C., a long dotted line 1042 represents the time-variation of the refractive index at the furnace temperature of 90° C., a dotted line 1043 represents the time-variation of the refractive index at the furnace temperature of 100° C., and a solid line 1044 represents the time-variation of the refractive index at the furnace temperature of 120° C. The first to third optical fibers and the optical fiber pieces are single mode optical fibers, and the refractive index n' of the cores thereof is set to 1.46.

In FIG. 12, each of the lines 1041 to 1044 varies where, after the refractive index temporarily decreases, the refractive index increases with time lapse, and then becomes constant after some time elapses. The time period from the start time of curing till the time when the refractive index becomes constant is different among the curves. When the degree of cure of the adhesive agent 1 is measured at the time point when the refractive index becomes constant, the degree of cure reaches a predetermined degree of cure. Accordingly, the time period from the start time of curing till the time when the refractive index becomes constant can be determined as a curing completion time for the adhesive agent 1. The curing completion time obtained from FIG. 12 is substantially coincident with the standard curing conditions described above.

As described above, according to the degree of cure measuring apparatus 1010 according to the third embodiment, the curing completion time for the adhesive agent can be measured with high precision by measuring the time-variation of the refractive index of the adhesive agent. Furthermore, according to the degree of cure measuring apparatus 1010, since the time-variation of the degree of cure of the adhesive agent can be measured, information as to how long it takes to cure the adhesive agent by about 50% of degree of cure can be obtained, for example.

The degree of cure measuring apparatus 1010 according to the third embodiment has the following advantages. When the degree of cure is measured while the tip face 1026a of the second optical fiber 1026 is in direct contact with the adhesive agent 1036, the tip face 1026a and the adhesive agent 1036 adhere to each other by the curing of the adhesive agent 1036. Therefore, when the degree of cure of another adhesive agent is measured after the above measurement, it is necessary to exchange the second optical fiber 1026 itself. However, according to this embodiment, since the light guide member 1034 adhering to the adhesive agent 1036 can be detached from the probe 1018, only the light guide member 1034 may be exchanged when the degree of cure of another adhesive agent is measured. Accordingly, according to the degree of cure measuring apparatus 1010 of this embodiment, the degrees of cure of plural kinds of adhesive agent can be inexpensively and easily measured.

As described above, a single mode optical fiber is preferably used as the optical fiber piece 1032 used for the light guide member 1034. Since the core diameter of the single mode optical fiber is equal to 10 μm or less, which is small, light other than light reflected from the interface between the second end face 1032b of the optical fiber piece 1032 and the adhesive agent 1036 (light which is temporarily incident into the adhesive agent 1036 and irregularly reflected and the like) is hardly incident into the core. Accordingly, the refractive index of the adhesive agent 1036 can be stably measured.

Figure 13:
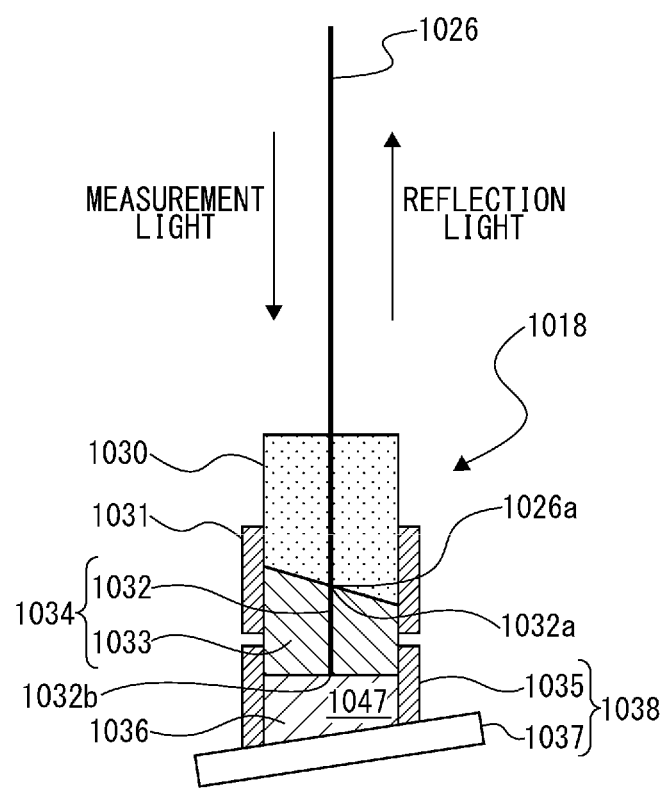
FIG. 13 is a diagram illustrating another modification of the probe.

FIG. 13 illustrates a modification of the probe. A probe 1018 according to this modification is different from the probe illustrated in FIG. 10 in that an adhesive agent holder 1038 for holding the adhesive agent 1036 is further provided. The adhesive agent holder 1038 has a cylindrical glass pipe 1035 inserted in the tip portion of the capillary piece 1033, and a glass plate 1037 provided to a tip portion of the glass pipe 1035.

The capillary piece 1033 is inserted in the glass pipe 1035 till a halfway position of the whole length of the glass pipe 1035. A space 1047 for holding the adhesive agent 1036 (referred to as adhesive agent holding space) is formed by an inner wall surface of the glass pipe 1035, the tip face of the capillary piece 1033 and the second end face 1032b of the optical fiber piece 1032. The glass plate 1037 is provided so as to block an opening of the adhesive agent holding space 1047, whereby the adhesive agent 1036 is enclosed in the adhesive agent holding space 1047.

In this modification, the adhesive agent 1036 is filled in the adhesive agent holding space 1047. Accordingly, the second end face 1032b of the optical fiber piece 1032 and the adhesive agent 1036 come into contact with each other. Under this state, the measurement light is applied from the second end face 1032b of the optical fiber piece 1032 to the adhesive agent 1036. This measurement light returns from the interface between the adhesive agent 1036 and the second end face 1032b to the optical fiber piece 1032, and is input to the optical splitter 1016 through the second optical fiber 1026.

According to this modification, the measurement can be performed while the adhesive agent 1036 is held in the probe 1018; therefore, the probe 1018 can be easily handled.

Figure 14:
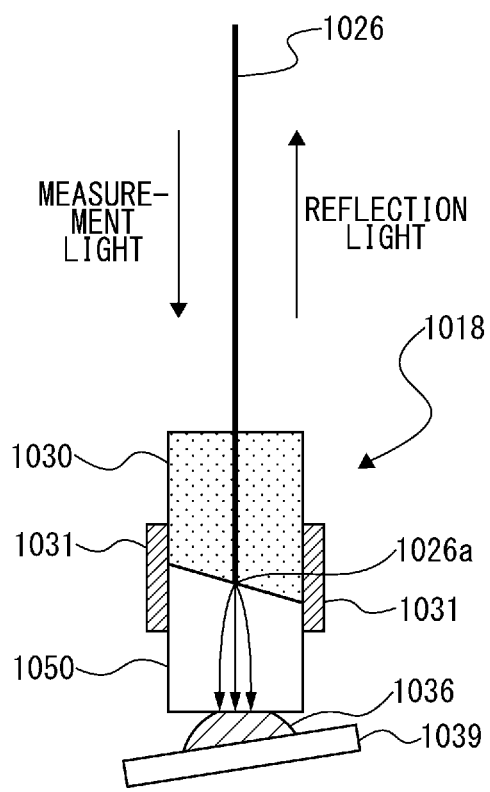
FIG. 14 is a diagram illustrating another modification of the probe.

FIG. 14 illustrates another modification of the probe. A probe 1018 illustrated in FIG. 14 is different from the probe illustrated in FIG. 10 in that a lens 1050 as a light guide member for guiding measurement light from the second optical fiber 1026 to the adhesive agent 1036 is provided. The lens 1050 is disposed so that an incident face thereof comes into contact with the tip face 1026a of the second optical fiber 1026. The incident face of the lens 1050 is configured as a slope surface in accordance with the tip face of the capillary 1030 and the tip face 1026a of the second optical fiber 1026.

The lens 1050 is configured so as to emit measurement light incident from the tip face 1026a of the second optical fiber 1026 as parallel light. The parallel light emitted from the lens 1050 returns from the interface between the lens 1050 and the adhesive agent 1036 to the lens 1050, and then is input to the detector 1020 through the second optical fiber 1026.

Also in this modification, the lens 1050 adhering to the adhesive agent 1036 can be detached from the probe 1018. Therefore, only the lens 1050 may be exchanged when the degree of cure of another adhesive agent is measured. Accordingly, the degrees of cure of plural kinds of adhesive agent can be measured inexpensively and easily.

Figure 15:
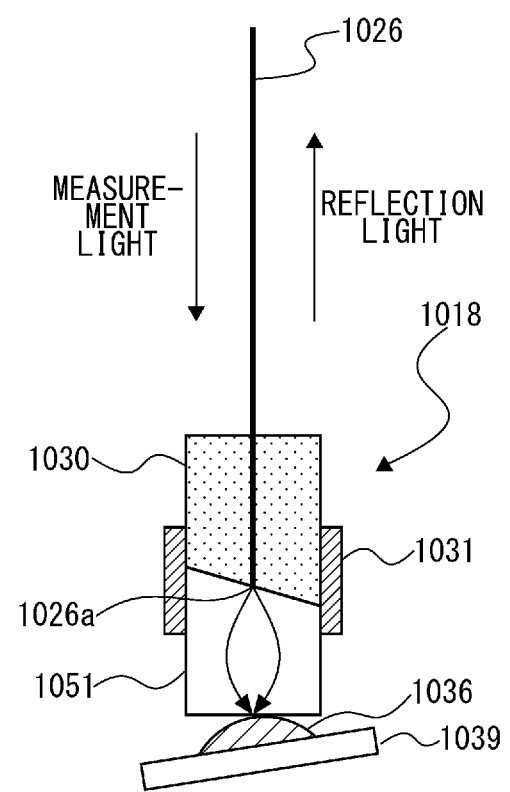
FIG. 15 is a diagram illustrating another modification of the probe.

FIG. 15 illustrates another modification of the probe. A probe 1018 illustrated in FIG. 15 is different from the probe illustrated in FIG. 10 in that a lens 1051 as a light guide member for guiding measurement light from the second optical fiber 1026 to the adhesive agent 1036 is provided. The lens 1051 is disposed so that an incident face thereof comes into contact with the tip face 1026a of the second optical fiber 1026. The incident face of the lens 1051 is configured as a slope surface in accordance with the tip face of the capillary 1030 and the tip face 1026a of the second optical fiber 1026.

The lens 1051 is configured so that measurement light incident from the tip face 1026a of the second optical fiber 1026 is focused onto a light emission face. The measurement light emitted from the lens 1051 returns from the interface between the lens 1051 and the adhesive agent 1036 to the lens 1051, and then is input to the detector 1020 through the second optical fiber 1026.

Also in this modification, the lens 1051 adhering to the adhesive agent 1036 can be detached from the probe 1018. Therefore, when the degree of cure of another adhesive agent is measured, only the lens 1051 may be exchanged. Accordingly, the degrees of cure of plural kinds of adhesive agent can be inexpensively and easily measured.

Figure 16:
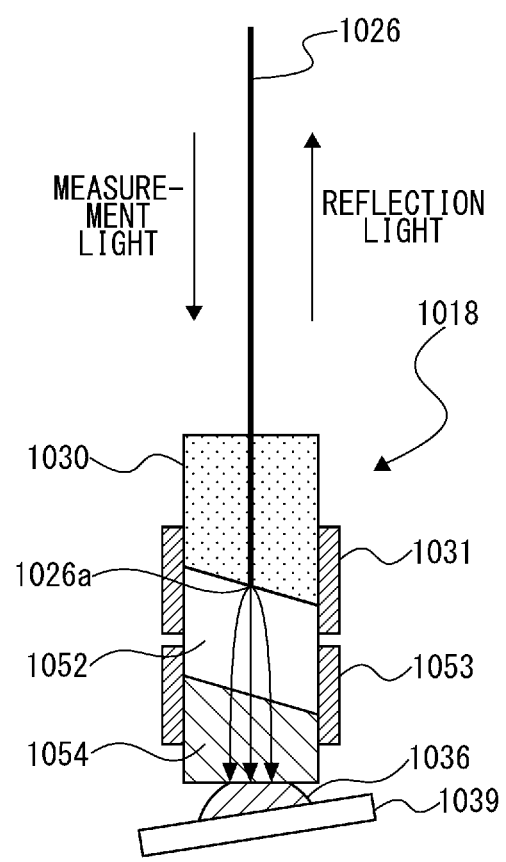
FIG. 16 is a diagram illustrating another modification of the probe.

FIG. 16 illustrates another modification of the probe. A probe 1018 illustrated in FIG. 16 is different from the probe illustrated in FIG. 10 in that a lens 1052 and a light guide part 1054 as light guide members for guiding measurement light from the second optical fiber 1026 to the adhesive agent 1036 are provided.

The lens 1052 is disposed so that an incident face thereof comes into contact with the tip face 1026a of the second optical fiber 1026. The lens 1052 and the capillary 1030 are connected to each other by a split sleeve 1031. The incident face of the lens 1052 is configured as a slope surface in accordance with the tip face of the capillary 1030 and the tip face 1026a of the second optical fiber 1026. The lens 1052 collimates light incident from the tip face 1026a of the second optical fiber 1026. The lens 1052 is configured so that measurement light incident from the tip face 1026a of the second optical fiber 1026 is emitted as parallel light from a light emission face of the light guide part 1054, as illustrated in FIG. 16.

The light guide part 1054 is disposed so that an incident face thereof comes into contact with a light emission face of the lens 1052. The light guide part 1054 is configured in a rod-like shape, and detachably connected to the lens 1052 by the split sleeve 1053. In order to prevent reflection, the connection face between the lens 1052 and the light guide part 1054 is configured as a slope surface. The light guide part 1054 is formed of a material having substantially the same refractive index as the adhesive agent 1036 before curing. When the degree of cure of the adhesive agent 1036 is measured, the light emission face of the light guide part 1054 is brought into contact with the adhesive agent 1036, and the adhesive agent 1036 is irradiated with light emitted from the lens 1052 under this state. Before the adhesive 1036 is cured, the refractive index of the light guide part 1054 and the refractive index of the adhesive agent 1036 are substantially equal to each other, and therefore there exits little reflection light returning from the interface between the light guide part 1054 and the adhesive agent 1036 to the second optical fiber 1026. However, when the adhesive agent 1036 is cured and the refractive index thereof varies, reflection light returning from the interface between the light guide part 1054 and the adhesive agent 1036 to the second optical fiber 1026 occurs. Accordingly, the degree of cure of the adhesive agent 1036 can be detected with high precision by detecting this reflection light.

In this modification, since the light guide part 1054 adhering to the adhesive agent 1036 can be detached from the probe 1018, only the light guide part 1054 may be exchanged when the degree of cure of another adhesive agent is measured. Accordingly, the degrees of cure of plural kinds of adhesive agent can be measured more inexpensively and easily.

FIGS. 17A and 17B are diagrams illustrating a degree of cure measuring method according to the third embodiment of the present invention. In this method, as illustrated in FIG. 17A, the tip face 1026a of the second optical fiber 1026 is first brought into contact with the adhesive agent 1036, and measurement light is emitted from the tip face 1026a of the second optical fiber 1026 to the adhesive agent 1036 under the above state. Thereafter, measurement light returning from the interface between the tip face 1026a of the second optical fiber 1026 and the adhesive agent 1036 to the second optical fiber 1026 is detected by using the detector 1020. After the degree of cure of the adhesive agent 1036 is measured, the tip portion of the second optical fiber 1026 adhering to the adhesive agent 1036 is cut by using a fiber cutter or the like. Then, the newly formed tip face 1026b of the second optical fiber 1026 is polished for next measurement.

According to the degree of cure measuring method, the tip portion of the second optical fiber 1026 adhering to the adhesive agent is cut out after the degree of cure is measured, whereby a new tip face for measuring the degree of cure of another adhesive agent can be formed on the second optical fiber 1026. According to this method, since an optical element such as a light guide member is unnecessary, the degree of cure of the adhesive agent can be measured more inexpensively.

Fourth Embodiment

Figure 18:
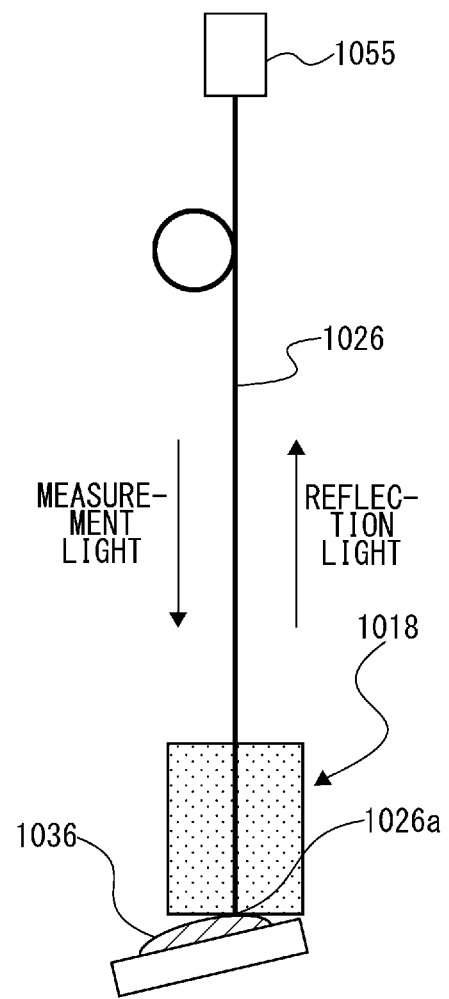
FIG. 18 is a diagram illustrating a degree of cure measuring method according to a fourth embodiment of the present invention.

FIG. 18 is a diagram illustrating a degree of cure measuring method according to a fourth embodiment of the present invention. First, a second optical fiber 1026 provided with a connector 1055 at an end portion thereof at the opposite side of the tip face 1026a is used in this method as illustrated in FIG. 18. The connector 1055 may be directly connected to the optical splitter 1016 or connected to a relay optical fiber connected to the optical splitter 1016.

In this method, first, the tip face 1026a of the second optical fiber 1026 is brought into contact with the adhesive agent 1036, and measurement light is emitted from the tip face 1026a of the second optical fiber 1026 to the adhesive agent 1036 under the above state as illustrated in FIG. 18. Thereafter, light returning from the interface between the tip face 1026a of the second optical fiber 1026 and the adhesive agent 1036 to the second optical fiber 1026 is detected by using the detector 1020. After the degree of cure of the adhesive agent 1036 is measured, the second optical fiber 1026 adhering to the adhesive agent 1036 is detached from the optical splitter 1016. Then, another second optical fiber is connected to the optical splitter 1016 for next measurement.

According to the degree of cure measuring method, the degree of cure of the adhesive agent can be measured more easily than the method described with reference to FIG. 17 by exchanging the whole second optical fiber 1026 adhering to the adhesive agent.

In the third and fourth embodiments described above, the degree of cure of the adhesive agent is measured by obtaining the time-variation of the refractive index. However, the degree of cure of the adhesive agent can be measured by obtaining the time-variation of light returning from the interface between the light guide member and the adhesive agent to the optical fiber.

The embodiments of the present invention are described above. It is understandable by persons skilled in the art that these embodiments are examples, various modifications may be made to the respective constituent elements and the combination of the respective processing processes, and these modifications are within the scope of the present invention.

For example, the laser diode may be blinked at a frequency of about 100 Hz to 10 kHz and only reflection light of these frequency components may be detected. For example, the detector is provided with a lock-in circuit, and the reflection light is detected in synchronization with the blinking of the laser diode 1012. In this case, the measurement can be performed with higher sensitivity without being affected by disturbance light.

Furthermore, a part of measurement light emitted from the laser diode may be monitored to offset variation of a detected light amount caused by variation of the light amount of the measurement light. In this case, the refractive index can be measured with higher precision.

Still furthermore, in the above embodiments, the laser diode (LD) is used as a light source. However, a light emitting diode (LED: Light Emitting Diode) may be used as a light source.

In the above embodiments, the present invention is applied to the degree of cure measuring apparatus for adhesive agent. However, the present invention is also applicable to measurement of the process of a reaction involving volume contraction.

What is claimed is:

1. A degree of cure measuring apparatus for measuring a degree of cure of adhesive agent, comprising:
   an optical fiber for emitting light from a tip face thereof;
   a light guide member detachably connected to the optical fiber and for irradiating the adhesive agent with light while a light emission face thereof is in contact with the adhesive agent; and
   a detector for detecting light returning from an interface between the light emission face of the light guide member and the adhesive agent to the light guide member, wherein
   the light guide member has a light guide part for irradiating the adhesive agent with light incident thereto while a light emission face thereof is in contact with the adhesive agent, and that is formed of a material having substantially the same refractive index as the adhesive agent before cure.

2. The degree of cure measuring apparatus according to claim 1, wherein
   the light guide member further has a lens provided between the optical fiber and the light guide part.

3. The degree of cure measuring apparatus according to claim 1, further comprising a refractive index calculator for calculating a refractive index of the adhesive agent from a rate of a light amount detected by the detector to an emission light amount from the light guide member.

4. The degree of cure measuring apparatus according to claim 3, further comprising a recorder for recording time-variation of the refractive index calculated by the refractive index calculator.

5. The degree of cure measuring apparatus according to claim 1, wherein
   the optical fiber is a single mode optical fiber.

6. The degree of cure measuring apparatus according to claim 1, wherein
   the light guide member has an adhesive agent holder for holding the adhesive agent.

7. The degree of cure measuring apparatus according to claim 1, further comprising:
   a capillary provided to a tip portion of the optical fiber; and
   a split sleeve for connecting the capillary and the light guide member.

* * * * *